United States Patent [19]

van der Knaap

[11] Plant 4,967

[45] Dec. 21, 1982

[54] CHRYSANTHEMUM NAMED DARK WESTLAND

[75] Inventor: Jacques C. M. van der Knaap, De Lier, Netherlands

[73] Assignee: Pan American Plant Company, Parrish, Fla.

[21] Appl. No.: 272,971

[22] Filed: Jun. 12, 1981

[51] Int. Cl.[3] ..... A01H 5/00

[52] U.S. Cl. ..... Plt./76

[58] Field of Search ..... Plt./76

*Primary Examiner*—Robert E. Bagwill

*Attorney, Agent, or Firm*—Chas. W. Rummler

[57] ABSTRACT

A new variety of a spider form chrysanthemum distinguished by its improved darker pink coloration when compared with its parent variety "Westland" (P.P. 4,589), particularly with respect to color retention, which is better than "Westland" which fades to a lighter pink more quickly. In all other respects, this sport of "Westland" is the same as its parent.

3 Drawing Figures

BACKGROUND OF THE INVENTION

My new cultivar of the spider type of chrysanthemum was discovered by me in 1976 as a sport in a field of "Westland" being grown by me in greenhouse at DeLier, Holland, for test and breeding purposes. The improved color of this sport and its much improved color retention led me to reproduce the sport for further observation, which I did by means of cuttings, at DeLier. Subsequently, this new variety was propagated through many successive generations, from which it was observed that the novel characteristics of the new plant would hold true from generation to generation and appeared to be firmly fixed. This new plant is now being propagated on a commercial scale, by means of cuttings, at Parrish, Fla., U.S.A.

DESCRIPTION OF THE DRAWINGS

This new chrysanthemum cultivar is illustrated by the accompanying drawings, of which sheet one is a print showing flowers of parent and mutant varieties which have been hand colored to show their true coloration, the new Dark Westland flower being at the right; sheet two is a mechanical reproduction of a photoprint of the front side of typical leaves of the new plant; and sheet three is a mechanical reproduction showing the back side of the same leaves.

DESCRIPTION OF THE NEW PLANT

The following is a detailed description of my new variety of chrysanthemum based upon observations of greenhouse plants made during the winter of 1980 at West Chicago, Ill., U.S.A., with color designations according to The R.H.S. Colour Chart published by The Royal Horticultural Society of London, England.

THE PLANT

Origin: Sport.

Parentage: "Westland," U.S. Plant Pat. No. 4,589.

Classification:

*Botanic.*—Chrysanthemum Morifolium.

*Commercial.*—Chrysanthemum for cut flowers.

Form: Perennial herbaceous bush.

Height: Varies from about 100 to 125 cm.

Growth: Vigorous and upright with good strength.

Branching character: Usual, under normal conditions.

Foliage:

*Quantity.*—Abundant with many leaves.

*Size of leaf.*—Length — To about 100 mm. Width — To about 70 mm.

*Shape of leaf.*—Lanceolate and lobed with slightly serrated margins.

*Surface texture.*—Canescent.

*Color.*—Upper side — 147A. Under side — 147B.

*Ribs and veins.*—Pinnate.

*Rachis.*—From about 30 to 100 mm. long.

*Petioles.*—Length — About 20 to 30 mm.

THE BUD

Form: Globular.

Size: The size varies from about 8 to 10 mm. in diameter and from about 6 to 8 mm. in depth.

Opening rate: The bud opens slowly.

Color of florets:

*When phyllaries first divide.*—74D on front and 74C on the reverse side.

*When florets begin to unfurl.*—The color is the same.

Phyllaries:

*Number.*—About 12.

*Shape.*—Lanceolate.

*Color.*—147B.

*Surface texture.*—Pubescent.

Peduncle or flower stem:

*Character.*—Erect and rigid.

*Length.*—About 40 to 150 mm.

*Aspect.*—Hairy.

*Color.*—138B.

THE FLOWER

Blooming habit: Intermittent, blooming profusely.

Natural season: Blooms once in the Fall.

Recommended flowering: Year around with photoperiod control.

Blooms:

*Form.*—Spider type with quill-shaped florets borne on a receptacle surrounded by an involucre of bracts.

*Shape.*—When bloom first opens — Cup-shaped. When bloom matures — Flat.

*Size.*—Medium. Diameter — About 80 cm. Depth — About 30 cm.

*Borne.*—As a cyme, being one of many carried in a racemose fashion on a strong, upright main stem.

Petalage:

*Phyllaries.*—About 12.

*Florets.*—About 150 in number.

*Arrangement.*—Imbricated.

*Form.*—Quill, with ragged and open apex and an entire type of margin.

*Texture.*—Soft.

*Appearance.*—Satiny.

*Color.*—Outer florets: Top Side — 74D. Reverse Side — 74C. Inner florets: Packed closely together and appearance to be darker, but are 74C from the tips to the yellow disc.

Flower stem:

*Character.*—Strong and upright.

*Length.*—About 40 to 150 mm.

*Color.*—146B.

Discoloration after full bloom: The flower fades slightly.

Persistence: Florets hang on and dry.

Fragrance: Typical chrysanthemum.

Lasting quality:

*On plant.*—About 4 weeks.

*As a cut flower.*—About 2 to 3 weeks. Recommended for greenhouse culture only.

REPRODUCTIVE ORGANS

Stamens: None present.

Pistils:

*Number.*—One for each ray floret.

*Styles.*—4 to 6 mm. long.

*Stigmas.*—Color — Yellow.

Ovaries: Inferior, bicarpellate.

The particular distinction of this new cultivar resides in the darker coloration of its flowers when compared to the color of "Westland". This is very apparent at cool temperatures but is not as apparent at extremely warm temperatures. The color retention is much better than that of "Westland", which fades to a lighter shade much more quickly. In all other aspects, this sport is the same as its parent "Westland".

I claim:

1. A new and distinct variety of chrysanthemum plant, substantially as herein shown and described, characterized by the spider form of its flowers with quill-shaped ray florets which are of a darker color than that of its parent and having a much better color retention character.

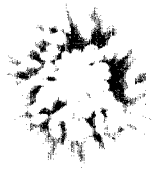
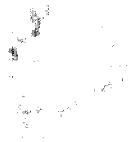

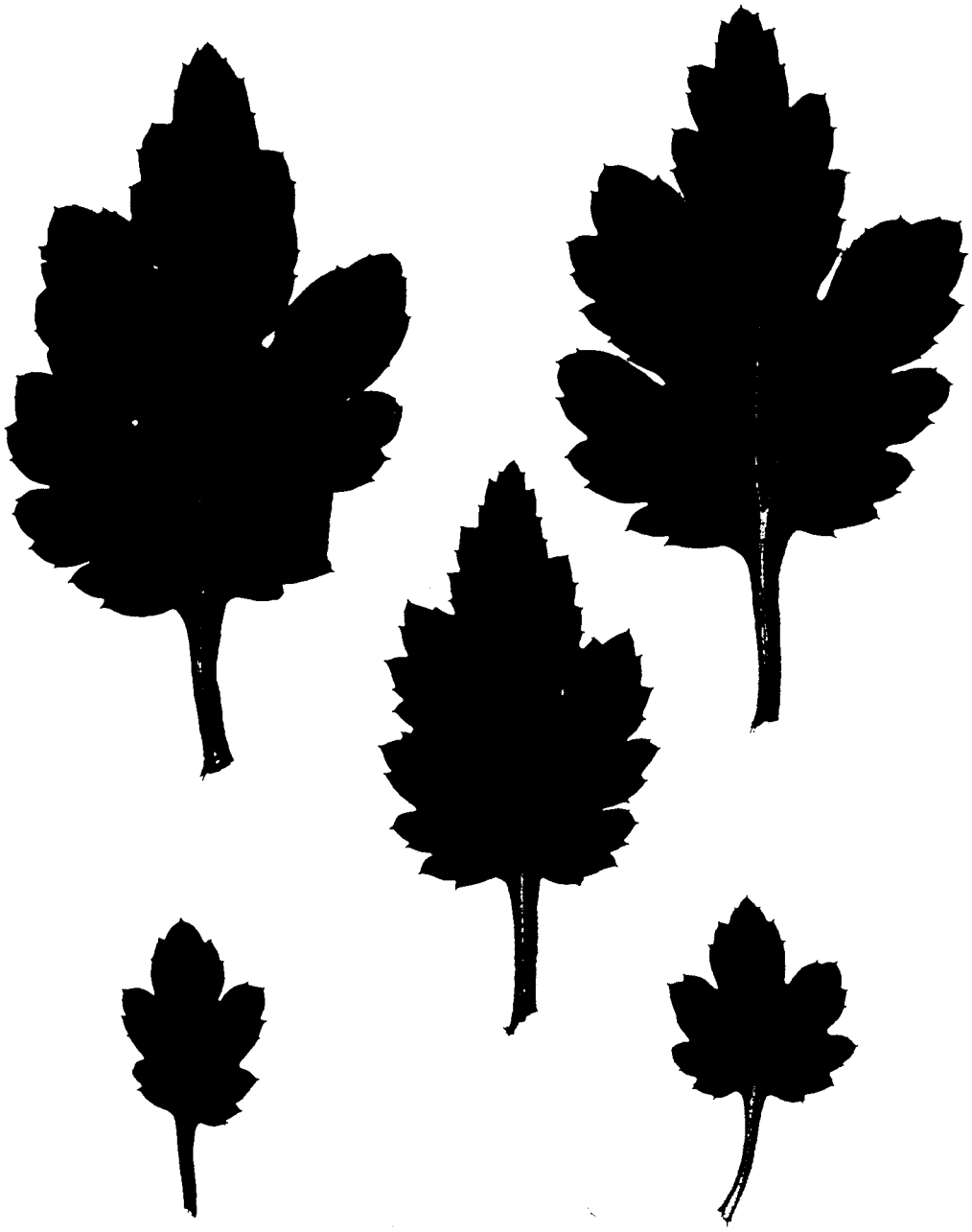

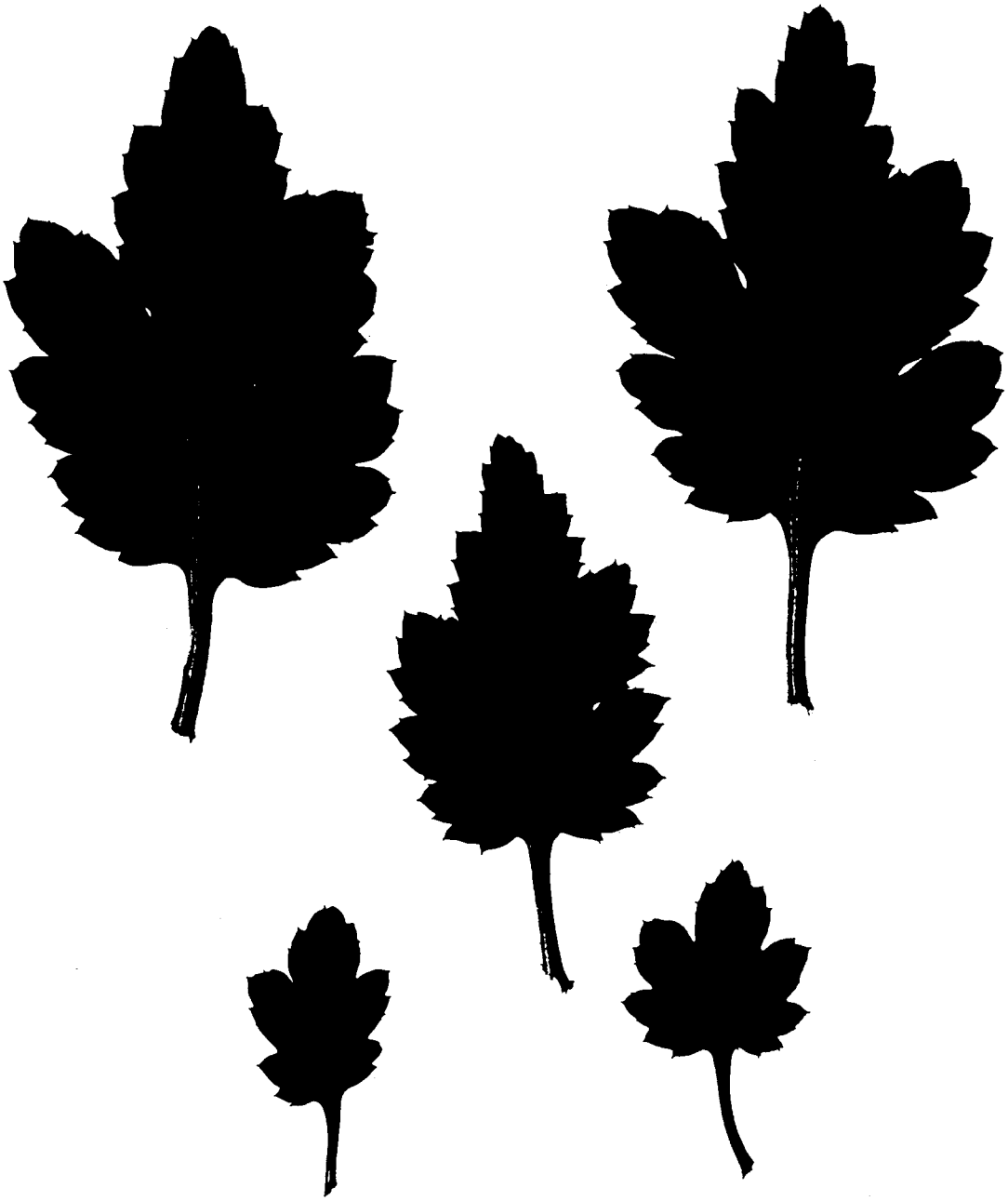

* * * * *